(12) United States Patent
Ghelli et al.

(10) Patent No.: US 8,066,942 B2
(45) Date of Patent: Nov. 29, 2011

(54) INTEGRATED DEVICE FOR HEATING AND OXYGENATING BLOOD IN AN EXTRACORPOREAL CIRCUIT

(75) Inventors: Nicola Ghelli, S. Pietro in Casale (IT); Edgardo Costa Maianti, Mirandola (IT); Roberto Balanzoni, San Giovanni Del Dosso (IT)

(73) Assignee: Eurosets S.r.l., Medolla (IT)

( * ) Notice: Subject to any disclaimer, the term of this patent is extended or adjusted under 35 U.S.C. 154(b) by 923 days.

(21) Appl. No.: 11/710,569

(22) Filed: Feb. 26, 2007

(65) Prior Publication Data
US 2007/0217948 A1    Sep. 20, 2007

(30) Foreign Application Priority Data
Mar. 17, 2006 (IT) .............................. MI2006A0490

(51) Int. Cl.
*A61M 37/00* (2006.01)
*A61M 1/00* (2006.01)
(52) U.S. Cl. ................... 422/45; 604/6.13; 604/6.14
(58) Field of Classification Search ............ 422/44–48; 604/4.01–6.16
See application file for complete search history.

(56) References Cited

U.S. PATENT DOCUMENTS

| 4,778,005 A * | 10/1988 | Smith ........................... 165/160 |
| 5,823,987 A * | 10/1998 | Elgas et al. .................. 604/6.13 |
| 6,004,511 A | 12/1999 | Biscegli |
| 2004/0175292 A1 * | 9/2004 | Ghelli et al. ................... 422/45 |
| 2006/0177343 A1 * | 8/2006 | Brian et al. ...................... 422/46 |

FOREIGN PATENT DOCUMENTS

| EP | 1 618 906 A | 1/2006 |
| WO | WO 97/33636 A | 9/1997 |

* cited by examiner

*Primary Examiner* — Leslie R. Deak
*Assistant Examiner* — Philip R Wiest
(74) *Attorney, Agent, or Firm* — Young & Thompson

(57) ABSTRACT

An integrated device for heating and oxygenating blood in an extracorporeal blood circuit, comprising a shell-and-tube heat exchanger module provided with a coupling to a blood supply line and with two couplings respectively for the intake and discharge of the water designed to exchange heat with the blood; ports are also provided for the passage of the blood toward an oxygenator module of the hollow-fiber type which is located at the peripheral region of the heat exchanger and is provided with a coupling to a blood discharge line; the device further comprises means adapted to direct the flow of blood along a turbulence-free path and with optimum distribution within the two modules.

8 Claims, 3 Drawing Sheets

INTEGRATED DEVICE FOR HEATING AND OXYGENATING BLOOD IN AN EXTRACORPOREAL CIRCUIT

The present invention relates to an integrated device for heating and oxygenating blood in an extracorporeal circuit.

BACKGROUND OF THE INVENTION

It is known that extracorporeal blood circuits in which blood is circulated during certain surgical procedures comprise, among other components, a heat exchanger, for keeping the temperature of the blood regulated by exchanging heat with a fluid normally constituted by water, and an oxygenator.

Very often, the two apparatuses are integrated into a single device, and the aim of the invention is to provide a device of this type which ensures that the blood flow has a turbulence-free path with optimum distribution in all regions and further provides high efficiency both in the exchange of heat between blood and water and in the exchange of oxygen with the blood.

SUMMARY OF THE INVENTION

The proposed aim is achieved by an integrated device for heating and oxygenating blood in an extracorporeal circuit according to the invention, which comprises a shell-and-tube heat exchanger module provided with a coupling to a blood supply line and with two couplings respectively for the intake and discharge of the water designed to exchange heat with the blood, ports being further provided for the passage of the blood toward an oxygenator module of the hollow-fiber type which is located at the peripheral region of said heat exchanger and is provided with a coupling to a blood discharge line, characterized in that it comprises means adapted to direct the flow of blood along a turbulence-free path and with optimum distribution within the two modules.

BRIEF DESCRIPTION OF THE DRAWINGS

Further characteristics and advantages will become better apparent from the description of two preferred but not exclusive embodiments of the invention, illustrated by way of non-limiting examples in the accompanying drawings, wherein.

DESCRIPTION OF THE PREFERRED EMBODIMENTS

Figure 1:
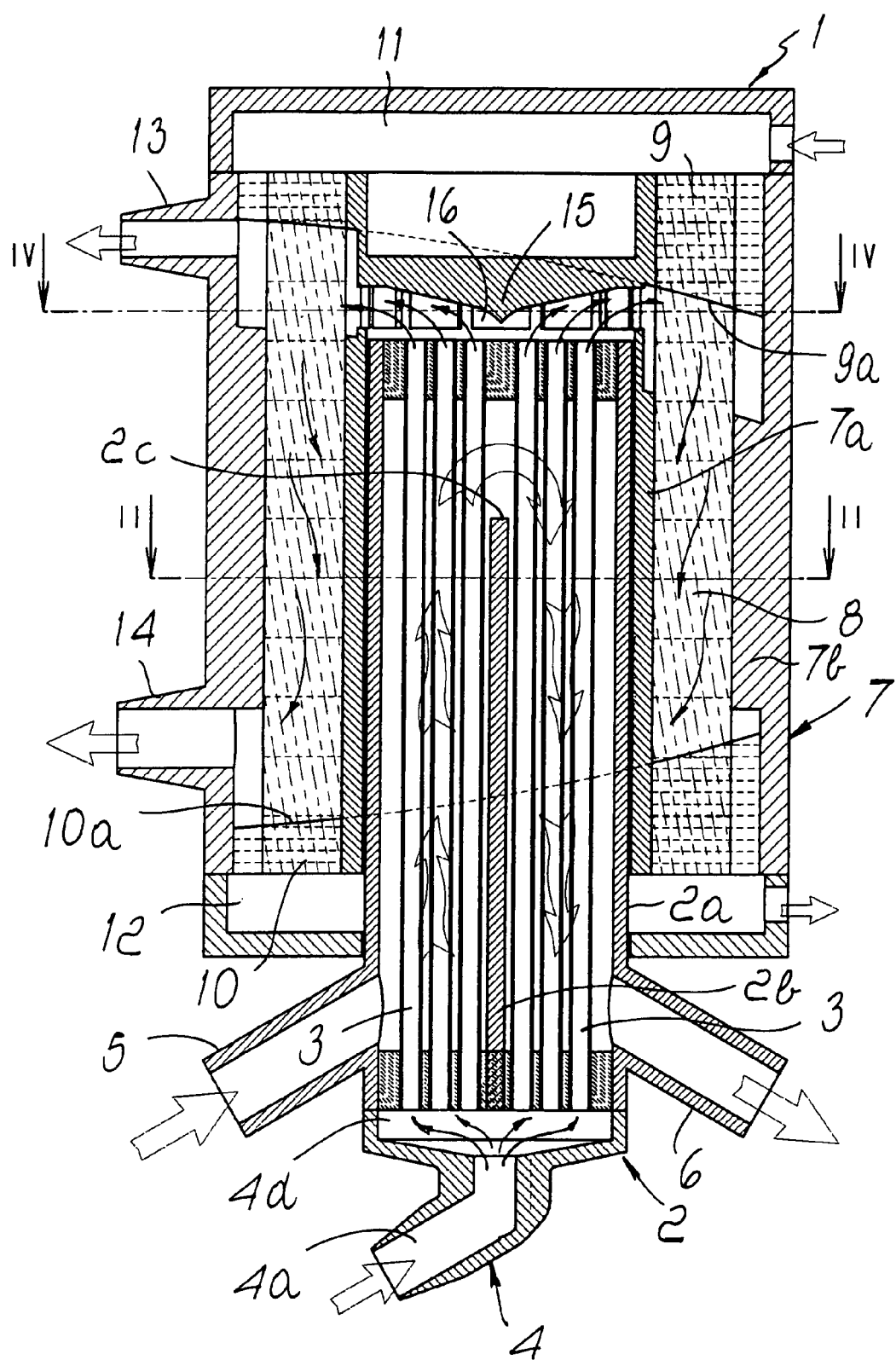
FIG. 1 is a longitudinal sectional view of the integrated device according to the invention.
Figure 2:
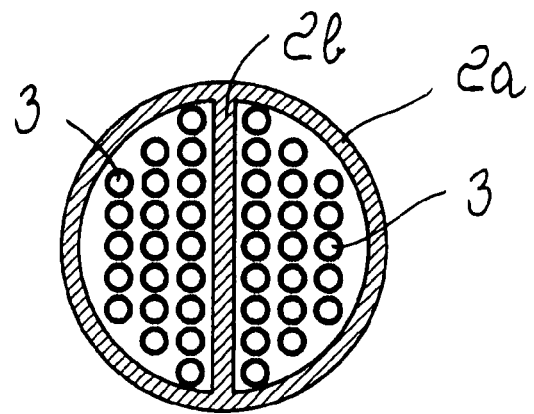
FIG. 2 is a partial sectional view, taken along the line II-II of FIG. 1.
Figure 3:
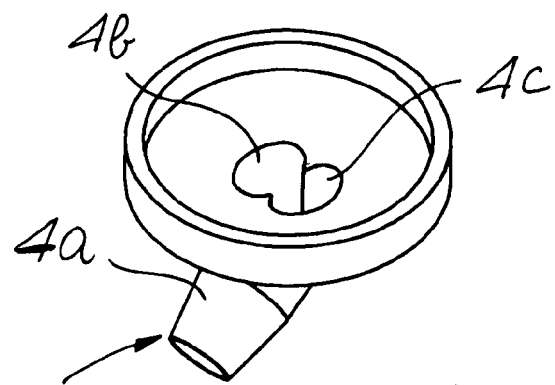
FIG. 3 is a view of a detail of the blood intake coupling.
Figure 4:
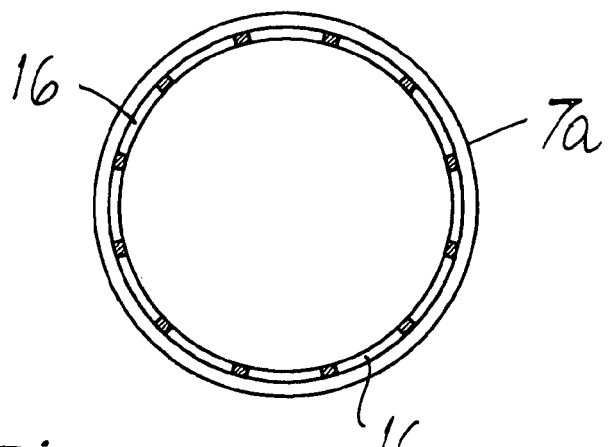
FIG. 4 is a partial sectional view, taken along the line IV-IV of FIG. 1.

With reference to the FIGS. 1 to 4, the reference numeral 1 generally designates the device according to the invention, which comprises a heat exchanger module, generally designated by the reference numeral 2, which in turn comprises, within an enclosure 2a, a shell-and-tube unit which is formed by tubes 3 which are designed to convey the blood that enters the device through a coupling 4 with a supply line and to be affected externally by the water that provides the heat exchange with the blood, in input by means of an intake coupling 5 and in output by means of a discharge coupling 6.

The enclosure 2a of the exchanger module 2 is inserted within an oxygenator module, generally designated by the reference numeral 7, more precisely a spooling core 7a around which there are, inserted in an annular portion of space 8 delimited toward the outside by an enclosure 7b, hollow fibers whose upper and lower ends are embedded respectively in the resin rings, known as potting, designated by the reference numerals 9 and 10; said fibers are intended, in a known manner, to convey oxygen from an intake compartment 11 to a discharge compartment 12.

The enclosure 7b of the oxygenator module is provided with a coupling 13 for removing bubbles from the blood and with a coupling 14 for connection to a line for the discharge of the blood from the device.

Observing now in detail the blood intake coupling 4, it can be seen that it has a first portion 4a which is cylindrical internally and tapered externally and is adapted to provide an easy connection to the blood supply line, and a second portion which is shaped like two lobes 4b, 4c and leads into a chamber 4d for accessing the shell-and-tube unit, thus providing an optimum distribution of blood which is divided uniformly among all the tubes of said shell-and-tube unit.

In output from the shell-and-tube unit, the blood reaches a chamber whose ceiling is shaped like a cusp-shaped diffuser 15 which is adapted to direct the flow toward the wall of said chamber and comprises consecutive and coplanar passage ports 16, which lead to the portion of space 8 which contains the hollow fibers which convey oxygen, all as shown by the arrows of FIG. 1, which illustrate a turbulence-free blood path with optimum distribution in all the regions of the device.

The discharge of the blood from the coupling 14 is furthermore facilitated by the inclination of a face 10a of the lower potting 10, while a suitable inclination of a face 9a of the upper potting 9 facilitates the discharge through the coupling 13 of bubbles contained in the blood.

Attention is now drawn to the exchanger module 2, which comprises a diametrical partition 2b, which lies parallel to the tubes 3 starting from the base and is interrupted at 2c, thus delimiting two chambers which are connected respectively to the intake coupling 5 and discharge coupling 6 for the water and are connected one another in the region above a top 2c of the partition 2b, in which the water follows the U-shaped path indicated by the arrows, partly in equicurrent and partly in countercurrent with respect to the flow of the blood in the tubes 3.

It should also be noted that the couplings 5 and 6 have the same inclination with respect to the axis of the device, thus offering conditions of particular convenience and interchangeability in connection to the water conveyance lines.

Figure 5:
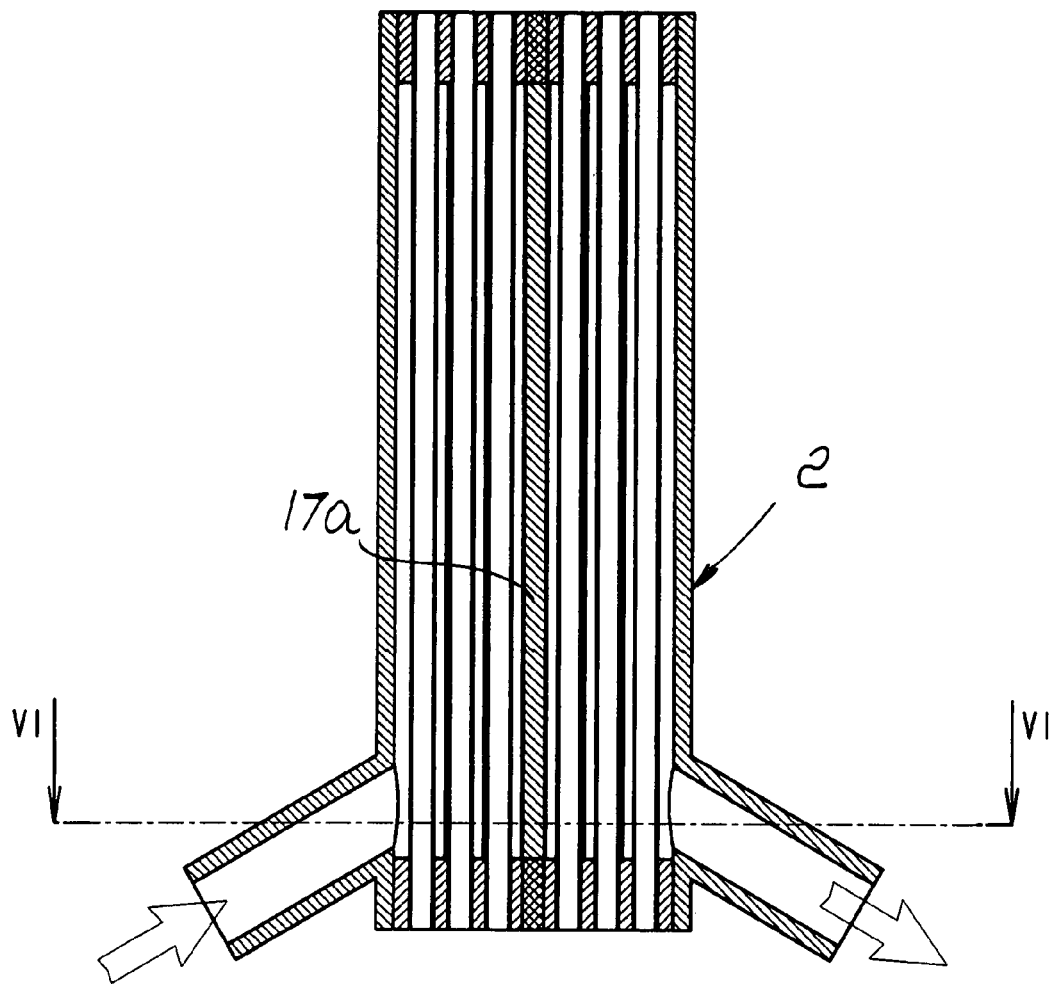
FIG. 5 is a view of the heat exchanger module according to another embodiment of the present invention.
Figure 6:
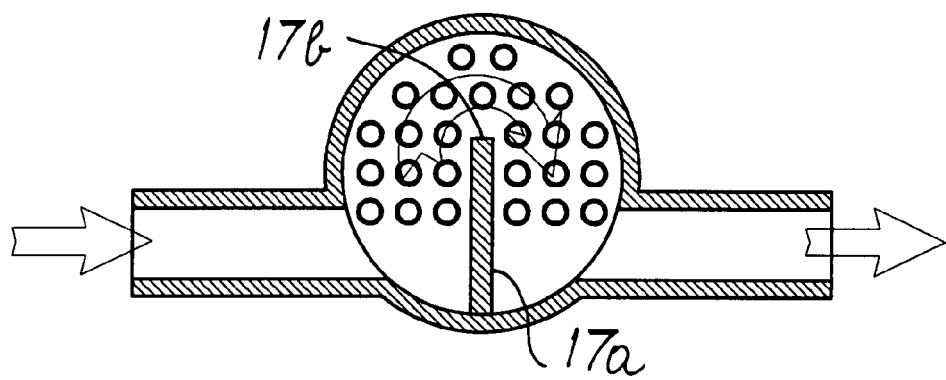
FIG. 6 is a sectional view, taken along the line VI-VI of FIG. 5.

FIGS. 5 and 6 illustrate another embodiment, generally designated by the reference numeral 17, of the heat exchanger module, which duplicates the shape of the previously described module 2 for all the elements except for a partition 17a, which extends parallel to the tubes of the shell-and-tube unit along their entire length and covers a partial portion of the diameter, being interrupted at 17b.

Two chambers are thus delimited which are connected respectively to the water intake and discharge couplings and are connected one another at the interruption 17b of the partition 17a, and the water traces a path which is indicated by the arrow of FIG. 6 in cross-flow with respect to the flow of blood in the tubes of the shell-and-tube unit.

The described invention is susceptible of numerous modifications and variations, all of which are within the scope of the appended claims; all the details may further be replaced with other technically equivalent elements.

The disclosures in Italian Patent Application No. MI2006A000490 from which this application claims priority are incorporated herein by reference.

What is claimed is:

1. An integrated device for heating and oxygenating blood, comprising a shell-and-tube heat exchanger module provided with a blood inlet coupling for connection to a supply line for blood and with two water couplings respectively for the intake and discharge of water for exchanging heat with the blood, the shell-and-tube heat exchanger module comprising an enclosure, and a plurality of tubes arranged within said enclosure for conveying the blood arriving from said blood coupling, each of said water couplings being arranged at a base of said enclosure such that entering water which enter said enclosure at said base of said enclosure flows directly about said plurality of tubes inside said enclosure adjacent said base, and such that exiting water exits said enclosure adjacent said base, said shell-and-tube heat exchanger module further comprising, arranged within the enclosure of said shell-and-tube heat exchanger module, a partition which extends parallel to the tubes and between different tubes of said plurality of tubes within said enclosure from the base of said enclosure, ports for passage of the blood toward an oxygenator module of a hollow-fiber type which is located at a peripheral region of said heat exchanger and is provided with a coupling to a blood discharge line, and a lower resin ring which comprises embedded lower ends of hollow fibers of the oxygenator module, a surface of said lower resin ring directed toward said oxygenator module being inclined so as to facilitate a motion of the blood module toward a discharge connector located proximate to a bottom of the oxygenator module.

2. The device according to claim 1, wherein the blood inlet coupling of the shell-and-tube heat exchanger module for connection with the supply line of the blood has a first portion which is internally cylindrical and tapers externally and is adapted to provide an easy connection to said supply line, and a second lobe-shaped portion which leads into a chamber for access to the shell-and-tube heat exchanger module.

3. The device according to claim 1, further comprising, at the ceiling of the chamber for the discharge of the blood from the shell-and-tube unit of the exchanger module, a cusp-shaped diffuser which is adapted to direct the flow of blood toward the wall of said chamber which comprises said ports for passage toward the oxygenator module which are consecutive and coplanar.

4. The device according to claim 1, comprising a bubble removal coupling for the blood which is located proximate to an upper lid of the oxygenator module, and an upper resin ring which comprises embedded upper ends of the hollow fibers of said oxygenator module, a surface of said upper resin ring directed toward said oxygenator module being inclined so as to facilitate discharge of the bubbles from the blood.

5. The device according to claim 1, wherein said partition is a diametrical partition which extends parallel to the tubes of the shell-and-tube heat exchanger module from the base of said enclosure, where said water couplings are provided, and along most of the length of said tubes, so as to delimit two chambers which are connected respectively to one of said water couplings and to the other of said water couplings and are connected to one another at a region located at a top of the shell-and-tube heat exchanger module.

6. The device according to claim 1, wherein said partition extends parallel to the tubes of the shell-and-tube heat exchanger module along their entire length and covers a partial portion of a diameter of said enclosure, so as to delimit two chambers which are connected respectively to one of said water couplings and to the other of said water couplings and are connected to one another at an interruption of the partition.

7. The device according to claim 1, wherein the two water couplings have a same inclination with respect to an axis of the device.

8. An integrated device for heating and oxygenating blood, comprising:
   a shell-and-tube heat exchanger module provided with a blood inlet coupling for connection to a supply line for blood and with two water couplings respectively for the intake and discharge of water for exchanging heat with the blood,
   the shell-and-tube heat exchanger module further comprising an enclosure, and a plurality of tubes arranged within said enclosure for conveying the blood arriving from said blood coupling,
   each of said water couplings being arranged at a base of said enclosure such that entering water which enter said enclosure at said base of said enclosure flows directly about said plurality of tubes inside said enclosure adjacent said base, and such that exiting water exits said enclosure adjacent said base,
   said shell-and-tube heat exchanger module further comprising, arranged within the enclosure of said shell-and-tube heat exchanger module, a partition which extends parallel to the tubes and between different tubes of said plurality of tubes within said enclosure from the base of said enclosure,
   ports for passage of the blood toward an oxygenator module of a hollow-fiber type which is located at a peripheral region of said heat exchanger and is provided with a coupling to a blood discharge line, and
   a bubble removal coupling for the blood which is located proximate to an upper lid of the oxygenator module, and
   an upper resin ring which comprises embedded upper ends of the hollow fibers of said oxygenator module, a surface of said upper resin ring directed toward said oxygenator module being inclined so as to facilitate discharge of the bubbles from the blood.

* * * * *